(12) United States Patent
Guo et al.

(10) Patent No.: US 11,406,517 B2
(45) Date of Patent: Aug. 9, 2022

(54) VASCULAR STENT

(71) Applicant: HANGZHOU ENDONOM MEDTECH CO. LTD., Zhejiang (CN)

(72) Inventors: Wei Guo, Zhejiang (CN); Yongsheng Wang, Zhejiang (CN); Jianmin Li, Zhejiang (CN); Guoqing Gao, Zhejiang (CN)

(73) Assignee: HANGZHOU ENDONOM MEDTECH CO. LTD., Hangzhou (CN)

( * ) Notice: Subject to any disclaimer, the term of this patent is extended or adjusted under 35 U.S.C. 154(b) by 0 days.

(21) Appl. No.: 16/764,154

(22) PCT Filed: Nov. 14, 2018

(86) PCT No.: PCT/CN2018/115416
§ 371 (c)(1),
(2) Date: May 14, 2020

(87) PCT Pub. No.: WO2019/096158
PCT Pub. Date: May 23, 2019

(65) Prior Publication Data
US 2020/0390575 A1    Dec. 17, 2020

(30) Foreign Application Priority Data

Nov. 17, 2017   (CN) .......................... 201711147217.5
Nov. 17, 2017   (CN) .......................... 201711147219.4

(51) Int. Cl.
*A61F 2/915*    (2013.01)
*A61F 2/82*    (2013.01)

(52) U.S. Cl.
CPC ........ *A61F 2/915* (2013.01); *A61F 2002/821* (2013.01); *A61F 2002/91508* (2013.01);
(Continued)

(58) Field of Classification Search
CPC ........ A61F 2002/821; A61F 2250/0039; A61F 2230/0067; A61F 2250/0037;
(Continued)

(56) References Cited

U.S. PATENT DOCUMENTS

2005/0209678 A1   9/2005  Henkes et al.
2007/0088428 A1   4/2007  Teichman
(Continued)

FOREIGN PATENT DOCUMENTS

CN    102068331 A    5/2011
CN    102462563 A    5/2012
(Continued)

OTHER PUBLICATIONS

The Supplementary European Search Report issued in corresponding application No. EP 18879329 dated Nov. 16, 2020, pp. 1-8, European Patent Office, Munich, Germany.
(Continued)

*Primary Examiner* — Rebecca S Preston
(74) *Attorney, Agent, or Firm* — Hauptman Ham, LLP (57) ABSTRACT

A vascular stent, including a plurality of wave-shaped supporters connected in an axial direction. The tubular stent includes a proximal support mechanism, a middle support mechanism, and a differential support mechanism connected in sequence; the middle support mechanism and the distal support mechanism are respectively closed-loop structure; the proximal support mechanism includes a first support portion connected to the middle support mechanism and a second support portion provided at the proximal end of the first support portion; the first support portion is a closed-loop structure; the second support portion is an open-loop structure, and the end surface of the proximal end of the second support portion is an uneven structure to provide local support in the circumferential direction.

19 Claims, 6 Drawing Sheets

(52) U.S. Cl.
CPC ............... *A61F 2002/91525* (2013.01); *A61F 2002/91541* (2013.01); *A61F 2002/91575* (2013.01); *A61F 2002/91583* (2013.01); *A61F 2210/0014* (2013.01); *A61F 2230/0013* (2013.01); *A61F 2230/0067* (2013.01); *A61F 2250/001* (2013.01); *A61F 2250/0006* (2013.01); *A61F 2250/0018* (2013.01); *A61F 2250/0037* (2013.01); *A61F 2250/0039* (2013.01); *A61F 2250/0098* (2013.01)

(58) Field of Classification Search
CPC .......... A61F 2/915–91583; A61F 2002/91583; A61F 2002/91575
See application file for complete search history.

(56) References Cited

U.S. PATENT DOCUMENTS

| | | | | |
|---|---|---|---|---|
| 2011/0288622 | A1* | 11/2011 | Chan | A61F 2/915 623/1.11 |
| 2012/0116500 | A1 | 5/2012 | Jang et al. | |
| 2012/0296362 | A1* | 11/2012 | Cam | A61F 2/915 606/191 |
| 2014/0277377 | A1* | 9/2014 | Ischinger | A61F 2/915 623/1.16 |
| 2014/0343666 | A1* | 11/2014 | Zhang | A61F 2/915 623/1.34 |

FOREIGN PATENT DOCUMENTS

| | | |
|---|---|---|
| CN | 204814293 U | 12/2015 |
| CN | 106456347 A | 2/2017 |
| CN | 206342572 U | 7/2017 |
| DE | 29904817 U1 | 5/1999 |
| EP | 0897700 A1 | 2/1999 |
| WO | 2006036319 A2 | 4/2006 |
| WO | 2017012673 A1 | 1/2017 |

OTHER PUBLICATIONS

International Search Report issued in International Application No. PCT/CN2018/115416, dated Feb. 18, 2019, pp. 1-7, State Intellectual Property Office of the P.R. China, Beijing, China.

* cited by examiner

VASCULAR STENT

CROSS REFERENCE TO RELATED APPLICATIONS

This application is the National Stage filing under 35 U.S.C. 371 of International Application No. PCT/CN2018/115416, filed on Nov. 14, 2018 and published as WO 2019/096158, which claims the priority and benefit of Chinese Application CN 201711147217.5, filed on Nov. 17, 2017, and Chinese Application CN 201711147219.4, filed on Nov. 17, 2017. The contents of all afore-mentioned applications are hereby incorporated by reference in their entireties.

TECHNICAL FIELD

Aspects of the present disclosure relate to the technical field of medical devices and particularly vascular stents. More specifically, certain implementations of the present disclosure relate to a vascular stent for treating a lesion near a vascular bifurcation.

BACKGROUND

For cardiovascular diseases such as vascular stenosis or occlusive lesion, a vascular stent is implanted to support the expansion of the blood vessel at the lesion, so that the blood flow of the blood vessel at the lesion is restored.

Figure 1A:
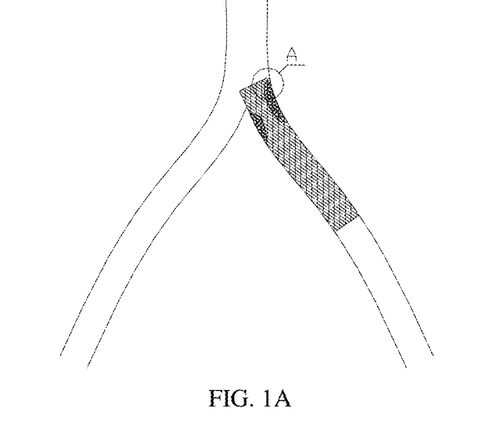
FIG. 1A and FIG. 1B are structural schematic diagrams of a vascular stent of the prior art implanted in a blood vessel.
Figure 1B:
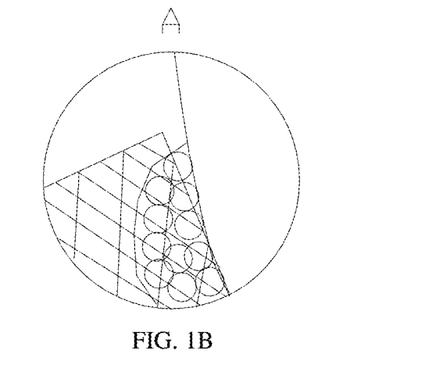

For ordinary lesions of vascular stenosis, a normal vascular stent can be inserted to support the blood vessel. However, some lesions of vascular stenosis are located near the vascular bifurcation (that is, the starting point of the branch blood vessel extending from the main blood vessel). At this time, the vascular stent needs to completely cover the lesion site. In some cases, vascular stents need to cover vascular areas other than the lesion site, such as adjacent lesion-free or almost lesion-free vascular areas, to support the blood vessels in an emergency or in the future. Therefore, when the lesion of vascular stenosis is located near the vascular bifurcation, the vascular stent must cover the mouth of the branch blood vessel. The mouth plane of the branch blood vessel is usually not perpendicular to the axially-extending plane of the branch blood vessel, because the branch blood vessel usually does not protrude from the main blood vessel at an angle of 90°, for example, from the main blood vessel at an angle between 40° and 60°. As shown in FIG. 1A and FIG. 1B, in this case, the ordinary stent cannot sufficiently cover the lesion site.

For example, the iliac vein compression syndrome is caused by venous adhesions, intimal hyperplasia, and fibrosis caused by continuous mechanical compression of the left common iliac vein with the right common iliac artery the fifth lumbar spine, and arterial pulsation, resulting in an disorder of the eft lower limb venous reflux. Therefore, the stent for the iliac vein needs a strong support force. As the vascular stent dedicated to veins is rarely provided in the market at present, in clinical operations the arterial vascular stent is mainly used to treat iliac vein stenosis, but the radial support of the arterial vascular stent is weak and cannot meet the demand. In addition, the iliac vein patch has a physiologically curved pelvic walk, so the corresponding vascular stent needs to have good flexibility. In addition, the bilateral iliac veins flowed upward into the inferior vena cava, showing an inverted "Y" shape. Specifically, the right iliac vein travels steeply and forms an angle of about 20 degrees with the inferior vena cava, and the left iliac vein forms an angle of about 40 degrees with the inferior vena cava. At present, the commonly used venous or peripheral vascular stent is a straight tubular stent. In addition, because the common left iliac vein is located between the right iliac artery and the lumbar spine, it is difficult to accurately locate and release the stent when it is implanted, and the stent is easy to jump forward into the inferior vena cava when the stent is released; the iliac vein involves the inferior vena cava lesion, and the stent needs to be protruded into the inferior vena cava for expansion, but the protruding stent may affect the blood reflux of the contralateral iliac vein and even cause contralateral iliac vein thrombosis. It has been reported that the incidence of unilateral stents into the inferior vena cava is 7-10%, resulting in a 15% incidence of contralateral popliteal vein thrombosis. In addition, there are clinical cases showing that the anterior wall of the iliac vein is due to the pulsation of the right iliac artery and is located in the occlusion site. The distal end of the iliac vein is often "funnel-shaped," the proximal end of the stent has too little access to the inferior vena cava, and the outer side of the stent cannot completely cover the iliac vein lesion; the straight tubular stent is easily squeezed to the distal end of the sacral vein due to insufficient anchoring force, resulting in treatment failure.

As shown in FIG. 1A, when the lesion of a vascular stenosis is located near the bifurcation of the blood vessel, the angle of the branch vascular bifurcation is not right. If one wants to completely cover the lesion, placing a stent in any branch blood vessel will partially protrude into the main blood vessel and the stent floating in the branch blood vessel of the main blood vessel will be unstable due to long-term scouring of the main blood vessel blood stream or the blood flow of the contralateral branch blood vessel. In addition, as shown in FIG. 1B, when a straight tubular stent is used at a bifurcation of a blood vessel, since the diameter of the branch blood vessel and the main blood vessel are greatly different, a large bend occurs at the bifurcation, so selecting a straight tubular stent is very likely to cause that turbulence or eddy current is formed due to the adverse effect of adherence on the opposite side of the blood flow, which will increase the risk of thrombosis in the stent.

SUMMARY

The technical problem to be solved by the present disclosure is, in light of the defects of the prior art, to provide a vascular stent for treating a vascular lesions near a vascular bifurcation, which can prevent the vascular stent from protruding into the main blood vessel and can cover and attach the lesion site well.

According to one aspect, the present disclosure provides a vascular stent including a plurality of wave-shaped supporters connected axially. The stent is tubular and includes a proximal support mechanism, a middle support mechanism, and a distal support mechanism connected in sequence; the middle support mechanism and the distal support mechanism are in a closed-loop structure, respectively; the proximal support mechanism includes a first support portion connected to the middle support mechanism and a second support portion provided on a proximal end of the first support portion; the first support portion is a closed-loop structure; and the second support portion is an open-loop structure, and an end surface of a proximal end of the second support portion is an uneven structure to provide regional support circumferentially.

According to another aspect, the end surface of the proximal end of the second support portion is an inclined plane, an inclined arc surface, or an inclined wave surface.

According to another aspect, the end surface of the proximal end is an inclined plane and an angle between the end surface of the proximal end and an axis of the vascular stent is α, where 90°>α>0°.

According to another aspect, the wave-shaped supporters of the proximal support mechanism have a same wavelength; peak units of adjacent wave-shaped supporters are connected to valley units to form grids; a number of grids of at least the second support portion gradually decreases from a distal end to a proximal end.

According to another aspect, an amplitude of the wave-shaped supporters of at least the second support portion gradually increases from an inside to an outside of the vascular stent.

According to another aspect, the middle support mechanism, the proximal support mechanism, and the distal support mechanism are connected by connecting components provided at a circumferential interval.

According to another aspect, the wave-shaped supporters of the middle support mechanism are connected by connecting components provided at a circumferential interval.

According to another aspect, the wave-shaped supporters include a plurality of supporting units; each supporting unit includes a peak unit, a valley unit, and a wave rod in connection between the peak unit and the valley unit; each connecting component includes at least one connecting rod; one end of the connecting rod is connected to the peak unit or the valley unit of a wave-shaped supporter and the other end of the connecting rod is connected to the wave rod of an adjacent wave-shaped supporter, or two ends of the connecting rod are respectively connected to a peak unit and a valley unit of two adjacent wave-shaped supporters.

According to another aspect, each connecting component includes at least two connecting rods, and two adjacent connecting rods are arranged in a shape of a figure eight expressed in Simplified Chinese or a shape of an inverted figure eight expressed in Simplified Chinese.

According to another aspect, projections of the connecting components provided between three adjacent wave-shaped supporters on a vertical axial plane do not overlap or partially overlap.

According to another aspect, the connecting rod is a straight rod, a special-shaped rod with a curved structure, a special-shaped rod with an arc structure, or a combination thereof.

According to another aspect, the wave rod is a straight rod, a special-shaped rod with a curved structure, a special-shaped rod with an arc structure, or a combination thereof.

According to another aspect, a part of two adjacent wave-shaped supporters not connected to the connecting component is suspended.

According to another aspect, after the vascular stent is expanded, at least an outer portion of the proximal support mechanism located at least outside the vascular stent gradually expands outwardly toward the vascular stent in a direction from the distal end to the proximal end.

According to another aspect, the proximal support mechanism expands outwardly toward the vascular stent to form an expansion portion, and an angle β between an outer contour of the expansion portion and the axis of the vascular stent satisfies: 30°≥β>0°.

According to another aspect, after the vascular stent is expanded, an outer diameter of the vascular stent gradually expands from the distal end to the proximal end to form a cone structure.

According to another aspect, a plurality of support points are provided on a proximal end of the stent proximal support mechanism and/or a distal end of the distal support mechanism.

According to another aspect, the support point is a hollow structure, and a radiopaque marker is provided inside the hollow structure.

The end surface of the proximal end of the vascular stent of the present disclosure is an uneven structure, which can provide local support in the circumferential direction; the inclination angle of the end surface of the proximal end of the uneven structure can be set according to the specific situation at the vascular bifurcation, which can prevent the vascular stent from protruding into the main blood vessel and can provide good coverage and attachment of the lesion area.

BRIEF DESCRIPTION OF THE DRAWINGS

The present disclosure will be further described below with reference to the drawings and embodiments.

DETAILED DESCRIPTION

In order to have a clearer understanding of the technical features, objects, and effects of the present disclosure, specific embodiments of the present disclosure will now be described in detail with reference to the accompanying drawings.

It should be noted that the following structure is a structure after the vascular stent is expanded.

Orientation definition: in the present disclosure, the proximal end refers to the end near the heart after the vascular stent is implanted into the blood vessel; the axial direction refers to the direction of the central axis of the vascular stent; the radial direction refers to the direction perpendicular to the central axis; the inner side of the stent refers to, when the stent is expanded, the side near the bifurcated vascular bifurcation, and the outer side of the sent refers to the other side of the stent relative to the inner side of the stent.

First Embodiment

Figure 2:
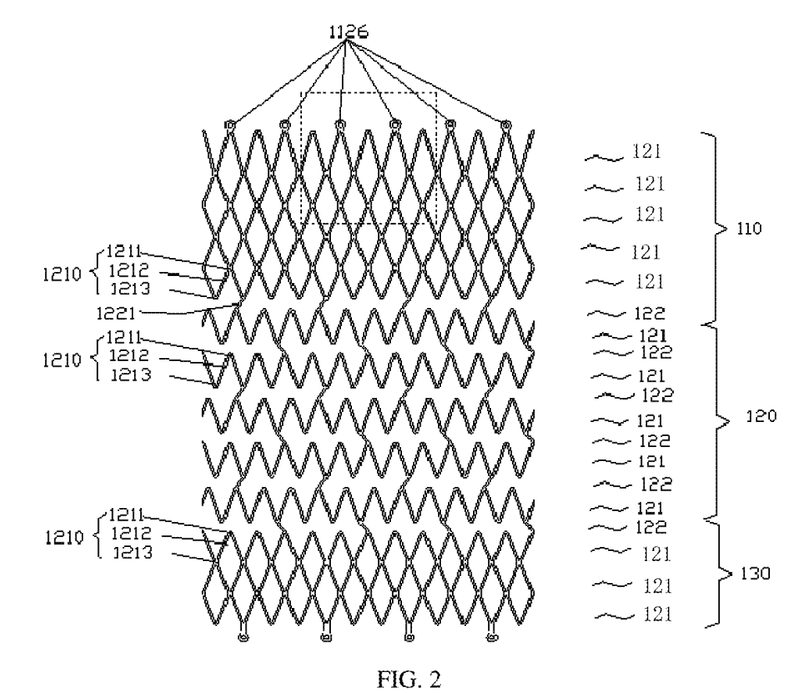
FIG. 2 is a structural schematic diagram of an expanded vascular stent in accordance with a first embodiment of the present disclosure.
Figure 2A:
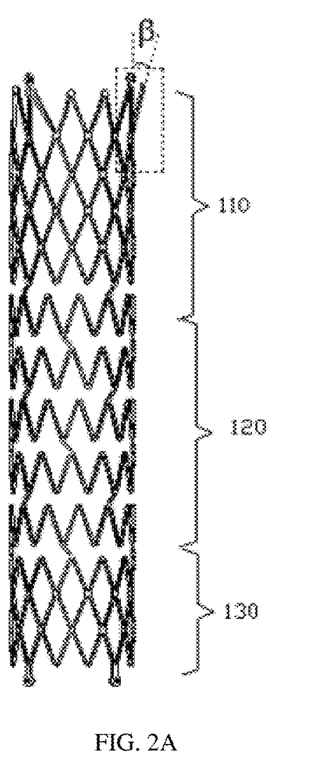
FIG. 2A and FIG. 2B are structural schematic diagrams of the vascular stent of FIG. 2 in different operating status.
Figure 2B:
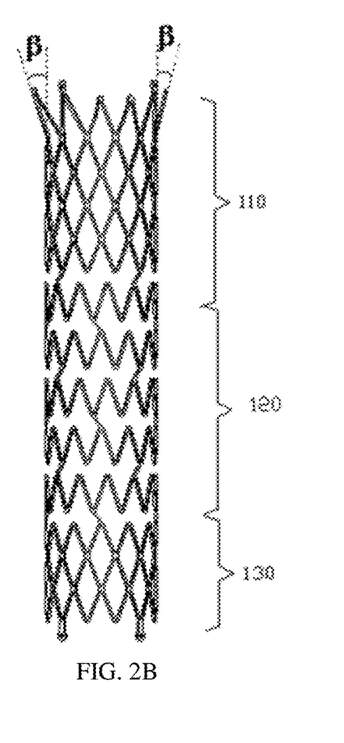

As shown in FIG. 2, FIG. 2A, and FIG. 2B, the vascular stent according to the first embodiment of the present disclosure is tubular and may be an equal-diameter structure; it may be a non-equal-diameter structure, such as a tapered tube structure; it may also be a changing-diameter structure composed of conical tube and straight tube. It is preferably a cone structure whose outer diameter gradually expands from the distal end to the proximal end after the vascular stent is expanded. The vascular stent according to the first embodiment of the present disclosure includes a proximal support mechanism 110, a middle support mechanism 120, and a distal support mechanism 130 which are disposed in sequence. The proximal support mechanism 110, the middle support mechanism 120, and the distal support mechanism 130 may be directly connected or connected by a connecting component 122.

The proximal support mechanism 110, the middle support mechanism 120, and the distal support mechanism 130 are all closed-loop structures. The closed-loop structure is projected as a closed loop on a vertical axial plane. The proximal support mechanism 110, the middle support mechanism 120, and the distal support mechanism 130 each includes a plurality of wave-shaped supporters 121 disposed along the axial direction.

Each wave-shaped supporter 121 includes a plurality of supporting units 1210 connected end to end. Each supporting unit 1210 includes a peak unit 1211, a valley unit 1213, and a wave rod 1212 connected between the peak unit 1211 and the valley unit 1213.

When the vascular stent is expanded into a plane, the shape of the wave rod 1212 is a straight rod, a special-shaped rod with a curved structure or a special-shaped rod with an arc structure, or a combination thereof. The special-shaped rod means that the wave rod 1212 is a non-straight rod, and the curved structure refers to the curved portion of the wave rod 1212. The curved portion can strengthen the bending or stretching performance of the wave rod 1212. The curved structure can be set at any position on the wave rod 1212, and is preferably set in the middle of the wave rod 1212. The special-shaped rod with a curved structure or an arc structure is an arc-shaped rod, a straight rod with an arc-shaped portion, a Z-shaped rod, or an S-shaped rod.

The wave rod 1212, the peak unit 1211, and the valley unit 1213 of each supporting unit 1210 are an integrated structure or a connection structure. The wave-shaped supporter 121 may also be an integrated structure or a connected structure. The vascular stent of the present disclosure is made by laser cutting and heat-setting a material. The material can be selected from stainless steel, tantalum, cobalt-based alloy, platinum, nickel-titanium alloy and new titanium alloy. The preferred material is nickel-titanium alloy.

The peak units 1211 and the valley units 1213 of adjacent wave-shaped supporters 121 are connected one-to-one to form grids. In this embodiment, the wave-shaped supporters 121 have the same wavelength and the same amplitude. The same wavelength means that the length of each waveform of the wave-shaped supporters 121 in the circumferential direction is the same. In other embodiments, the waveform of the wave-shaped supporters 121 may also be different, that is, it is not necessary to limit the amplitude of the waveform. The wavelength of each waveform of the wave-shaped supporters 121 only need to make that the peak units 1211 and the valley units 1213 of axially adjacent wave-shaped supporters 121 are connected one-to-one to form grids.

In this embodiment, the proximal support mechanism 110 is an even structure at end surfaces. At least the outer portion of the proximal support mechanism 110 located outside the vascular stent extends gradually from the distal end toward the proximal end toward the outer side of the stent. After the vascular stent is implanted into a branch blood vessel, the outer portion of the proximal support mechanism 110 or the entirety of the proximal support mechanism 110 gradually expands outward, which improve the apposition of the vascular stent. The outer portion refers to the portion of the wave-shaped supporter 121 extending away from the side where the blood vessel intersects and extending a length in the circumferential direction. The specific width of the outer portion and the angle of outward turning can be determined based on factors such as the actual diameter of the branch blood vessel, the difference in diameters between the branch blood vessel and the main blood vessel, and so on. As shown in FIG. 2 and FIG. 2A, a portion surrounded by a dotted line is an outer portion. As shown in FIG. 2A, the outer portion of the proximal support mechanism 110 gradually expands outward, and extends to the outside of the vascular stent to form an expansion portion. The angle β between the outline of the expansion portion and the axis of the vascular stent satisfies: 30°≥β≥0°. In this embodiment, β is preferably 30°. As shown in FIG. 2B, in other embodiments, the entirety of the proximal support mechanism 110 gradually extends toward the outer side of the stent to form a bell mouth-shaped expansion portion. The angle β between the outward turning expansion portion and the axis of the vascular stent is 20°.

The distal support mechanism 130 is formed by a plurality of axially connected wave-shaped supporters 121 of the supporting units 1210 having the same wavelength, and the peak units 1131 and the valley units 1121 of adjacent wave-shaped supporters 121 are connected one by one to form grids. The grids of the distal support mechanism 130 have the same structure as those of the first support portion 111 of the proximal support mechanism 110, and are not repeated here.

A plurality of support points 1126 may be provided at the proximal end of the proximal support mechanism 110 and the distal end of the distal support mechanism 130. The support points 1126 have a smooth convex structure provided on the peak units 1211 of the wave supporters 100, and may be a solid structure or a structure with a hole in the center. The number and interval of support points 1126 are set according to actual needs, and are not limited here. In this embodiment, the central hole of the support points 1126 is filled with a developing material to form a radiopaque marker for developing the position of the vascular stent in the blood vessel during surgery. The radiopaque marker can also be set at other positions on the ends of the proximal support mechanism 110 and the distal support mechanism 130.

In this embodiment, the middle support mechanism 120, the proximal support mechanism 110, and the distal support mechanism 130 are connected by connecting components 122 which are arranged along the circumferential direction by intervals. The supporting units 1210, which are not connected with the connecting components 122, of the wave-shaped supporters 121 are suspended, that is, there is no connection or suspension between the peak unit 1211 and the valley unit 1213 of the axially adjacent supporting units 1210 which are not connected to the connecting components 122.

In this embodiment, the axially adjacent wave-shaped supporters 121 in the middle support mechanism 120 are also connected by connecting components 122 arranged along the circumferential direction by intervals. Two adjacent wave-shaped supporters 121 without the connecting component 122 are not connected or suspended.

Two axially adjacent wave-shaped supporters 121 are not connected or suspended between two adjacent connecting components 122. No connection means that there is no connection between the peak unit 1211 of the wave-shaped supporter 121 and the axially adjacent valley unit 1213, so that two adjacent wave-shaped supporters 121 have a relatively large moving or bending space in the radial and axial directions, thereby increasing the flexibility of the vascular stent.

Each connecting component 122 includes at least one connecting rod 1221. There are various ways to connect the connecting rod 1221 and the corresponding supporting unit 1210. Both ends of the connecting rod 1221 can be connected to the axially adjacent peak unit 1211 and the valley unit 1213; one end of the connecting rod 1221 is connected to the peak unit 1211 or the valley unit 1213 of a wave-shaped supporter 121, and the other end of the connecting rod 1221 is connected with an axially adjacent wave rod 1212. In this embodiment, two ends of the connecting rod 1221 are connected to axially adjacent peak unit 1211 and valley unit 1213.

In this embodiment, the connecting rod 1221 and the corresponding supporting unit 1210 are an integrally formed structure or a connecting structure. Among them, integrated forming is made by laser cutting of the tube. Because two wave-shaped supporters 121 adjacent to the middle support mechanism 120 are not synchronous, i.e., the peak unit 1211 of one wave-shaped supporter 121 and the valley unit 1213 of an axially adjacent wave-shaped supporter 121 are staggered. The connecting rod 1221 is inclinedly connected between the axially adjacent peak unit 1211 and the valley unit 1213. The circumferentially adjacent connecting rods 1221 may be arranged in parallel or non-parallel, that is, the circumferentially adjacent connecting rods 1221 are arranged in a a shape of a figure eight expressed in Simplified Chinese or a shape of an inverted figure eight expressed in Simplified Chinese.

The arrangement of the connecting rods 1221 between two adjacent wave-shaped supporters 121 in the circumferential direction is the same or repeated according to certain rules.

The projections on the plane in the vertical axial direction by the connecting components 122 between two axially adjacent circles do not overlap or partially overlap. The connecting components 122 are spirally arranged or staggered in the axial direction. Spiral arrangement means that the axially adjacent connecting components extend in a spiral arrangement, and staggered arrangement means that the peaks and valleys connected by the axially adjacent connecting components are not on the same axis. The connecting rods 1221 are evenly distributed in groups along the circumferential direction, and the connecting rods 1221 between three adjacent wave-shaped supporters 121 are staggered in the axial direction, so that the connecting component 122 can withstand greater local tension and pressure, making the vascular stent expand or contract with uniform deformation.

The connecting rod 1221 is a straight rod, a special-shaped rod with a curved structure or a special-shaped rod with an arc structure, or a combination thereof. In this embodiment, the connecting rod 1221 is a straight rod.

The connecting components 122 disposed between the adjacent wave-shaped supporters 121 of the middle support mechanism 120, the connecting component 122 disposed between the proximal support mechanism 110 and the middle support mechanism 120, or the connecting component 122 disposed between the middle support mechanism 120 and the distal support mechanism 130 can be the same or can be different.

Second Embodiment

Figure 3:
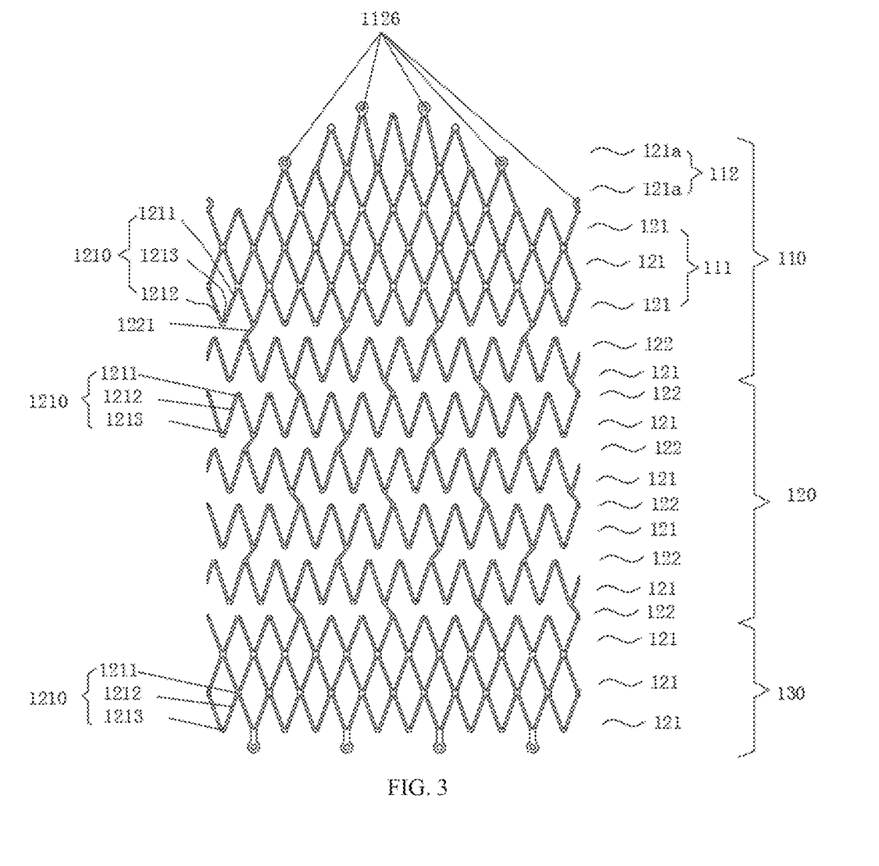
FIG. 3 is a structural schematic diagram of an expanded vascular stent in accordance with a second embodiment of the present disclosure.
Figure 3A:
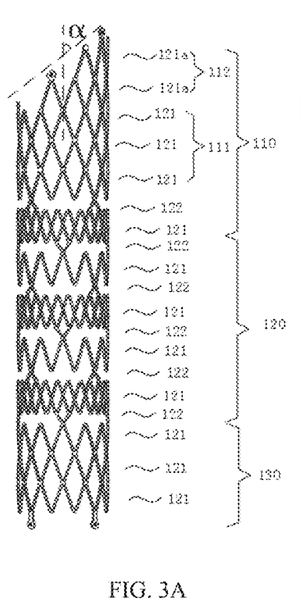
FIG. 3A, FIG. 3B, and FIG. 3C are structural schematic diagrams of the vascular stent of FIG. 3 in different operating status.
Figure 3B:
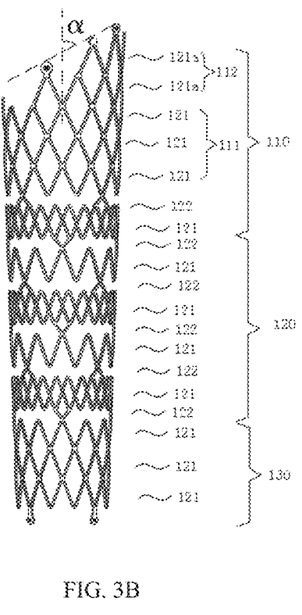

Please refer to FIG. 3, FIG. 3A, FIG. 3B, and FIG. 3C, the vascular stent of the second embodiment is basically the same as that of the first embodiment and has a tubular shape. After the vascular stent is expanded, it can be an equal-diameter structure, as shown in FIG. 3A; it can also be a non-equal-diameter structure, such as a tapered tube structure, as shown in FIG. 3B.

The differences are that the proximal end of the proximal support mechanism 110 is an uneven structure, which can provide circumferential local support, which makes the vascular stent not only adhere well but also cover the lesion site without protruding the main blood vessel. The proximal support mechanism 110 includes a first support portion 111 connected to the middle support mechanism 120 and a second support portion 112 provided at the proximal end of the first support portion 111. The first support portion 111 is a closed-loop structure. The number of grids of the second support portion 112 gradually decreases from the distal end to the proximal end, so that the second support portion 112 is an open-loop structure. Open-loop refers to the separation of the head and tail of the wave-shaped supporter 121a, that is, the wave-shaped supporter 121a is adjacent end-to-end or is spaced from each other at a certain distance, and the projection in the plane of the vertical axis is approximately C-shaped. The first support portion 111 includes a plurality of wave-shaped supporters 121 disposed along an axial direction. The second support portion 112 includes a plurality of wave-shaped supporters 121a disposed in the axial direction.

Because the end surface of the proximal end of the second support portion 112 is not even, the axial length of each position in the radial direction is different, so that the second support portion 112 can provide local support. The end surface of the proximal end of the second support portion 112 is not even, that is, the axial length of each position of the second support portion 112 in the circumferential direction is different. The end surface of the proximal end refers to the surface nearest to the proximal end of the vascular stent. The vascular stent is a tubular structure, and its end surface of the proximal end is annular. Since the proximal end of the second support portion 112 is not even, the inclined or zigzag proximal end is formed, that is, the non-even structure of the second support portion 112 has various forms. Corresponding to the shape of the branch blood vessel near the vascular bifurcation, the proximal end of this embodiment adopts an inclined structure. After the vascular stent is expanded, the end surface of the proximal end of the second support portion 112 is an inclined plane, arc, or wave surface. The second support portion 112 gradually extends from the radially inner side to the outer side of the first support portion 111. The equidistant extension length forms an inclined plane, and the non-equidistant extension forms an arc surface or a wavy surface. In this embodiment, it is preferable to extend at an equal distance, and the end surface of the proximal end is an inclined plane. The difference between the height of the outermost and innermost sides of the second support portion 112 is 0-30 mm, preferably 5-20 mm. The angle α between the inclined plane and the axis of the vascular stent satisfies: 90°>α>0°, preferably 60°>α>30°. The specific inclination angle is set according to the branch angle of the branch blood vessel and the diameter of the blood vessel, which is not limited herein.

The non-even structure can configure the inclination angle of the proximal end of the vascular stent according to the bifurcation of the branch blood vessel, so that the proximal end of the proximal support mechanism 110 and the position of the vascular bifurcation fit completely without protruding into the main blood vessel. In the prior art, the problem that the vascular stent cannot completely cover the lesion after implantation into the branch blood vessel and penetrates into the main blood vessel to affect the complications caused by the contralateral blood flow is avoided.

Figure 3C:
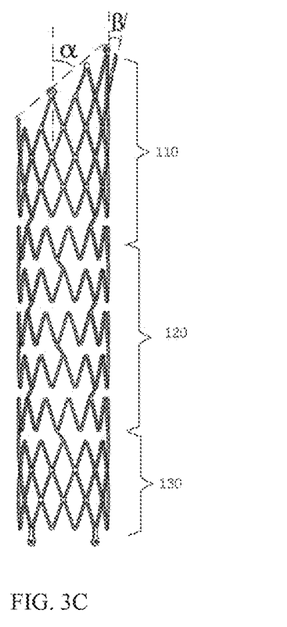

As shown in FIG. 3C, the second support portion 112 extends from the first support portion 111 in the axial direction to the proximal direction, and also gradually extends outward in the radial direction to form an inverted bell mouth structure. The degree of outward turning should not be too large. It is preferred that the expansion portion formed by extending and expanding outward to the vascular stent is located at the proximal end of the second support portion 112, and the expansion portion is preferably located at the longest portion of the second support portion 112. That is, at least an outer portion of the second support portion 112 has an expansion portion, and an angle β between the outline of the expansion portion and the axis of the vascular stent satisfies: 30°≥β>0°, that is, the angle β between at least the longest portion of the second support portion 112 and the axis of the vascular stent satisfies: 30°≥β>0°, and the second support portion 112 is turned slightly outward. As shown in FIG. 3C, in this embodiment, the angle β of the proximal support mechanism 110 gradually expanding outward in the radial direction from the distal end to the proximal end is 20°. Expansion of the proximal end of the proximal support mechanism 110 by a certain angle is more in line with the anatomy of the bifurcation blood vessel, so that the proximal end of the proximal support mechanism 110 achieves a good adherence effect.

Third Embodiment

Figure 4:
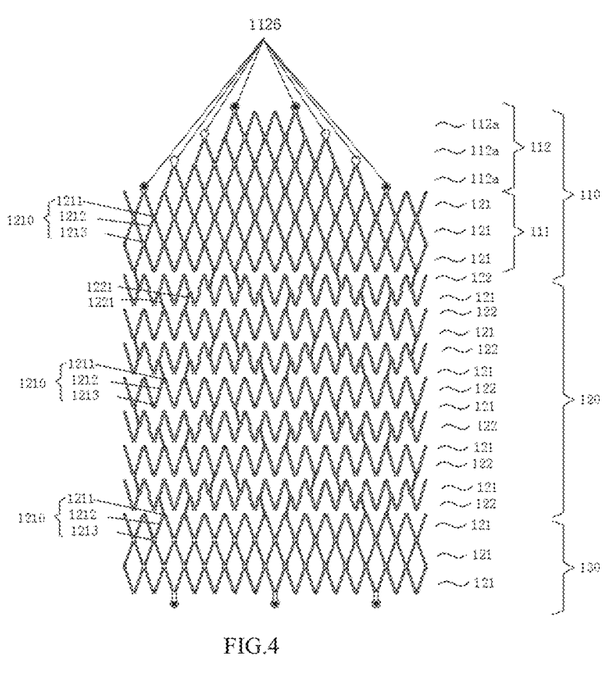
FIG. 4 is a structural schematic diagram of an expanded vascular stent in accordance with a third embodiment of the present disclosure.
Figure 4A:
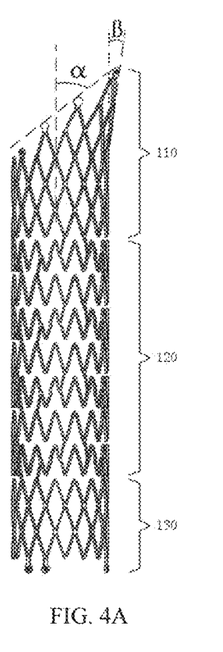
FIG. 4A is a structural schematic diagram of the vascular stent of FIG. 4 in an operating status.

As shown in FIG. 4 and FIG. 4A, the vascular stent of the third embodiment is based on the second embodiment, and is partially improved.

The vascular stent according to the second embodiment of the present disclosure has a tubular shape and includes a proximal support mechanism 110, a middle support mechanism 120, and a distal support mechanism 130 connected in sequence.

The differences are that each connecting component 122 is provided with at least two connecting rods 1221, and one end of each connecting rod 1221 is connected to a peak unit 1211 or a valley unit 1213 of a wave-shaped supporter 100, and the other end of each connecting rod 1221 is connected to a wave rod 1212 of an adjacent wave-shaped supporter. The connecting rods 1221 in each connecting component 122 can be arranged in parallel, and can also be arranged in a shape of a figure eight expressed in Simplified Chinese or a shape of an inverted figure eight expressed in Simplified Chinese. It is preferably arranged in a zigzag shape or an inverted zigzag shape to improve the radial supporting force. The two connecting rods 1221 of each connecting component 122 of the middle support mechanism 120 form a closed-loop connection unit with the supporting unit 1210 of the adjacent wave-shaped supporter 100. The closed-loop connection unit is evenly arranged between two adjacent wave-shaped supporters 121 along the circumferential direction and staggered between two adjacent wave-shaped supporters 121 along the axial direction, so that the vascular stent has good flexibility, scalability, and connection strength, and keeps the shape of the vascular stent and wave-shaped supporter in good shape during bending or expanding. Since the peak unit 1211 of the wave-shaped supporter 121 is facing the peak unit 1211 of the adjacent supporter 100 in the axial direction, the valley unit 1213 of the wave-shaped supporter 121 connected at the proximal end and the connecting rod 1221 on the wave rod 1212 of the wave-shaped supporter 121 connected at the distal end are inclined, that is, two connecting rods 1221 of each connecting component 122 are symmetrically arranged in are arranged in a shape of a figure eight expressed in Simplified Chinese or a shape of an inverted figure eight expressed in Simplified Chinese.

The connecting rod 1221 of the connecting component 122 is arranged in the same manner in the circumferential direction. The same arrangement means that the two connecting rods 1221 of each connecting component 122 are arranged in a a shape of a figure eight expressed in Simplified Chineseor a shape of an inverted figure eight expressed in Simplified Chinese. Preferably, the connecting components 122 disposed between three adjacent wave-shaped supporters 121 do not overlap or partially overlap in a projection on a vertical axial plane.

The difference is that the wave rods 1212 of the proximal support mechanism 110 and the distance support mechanism 130 both use straight rods, and the wave rod 1212 of the middle support mechanism 120 selects a special-shaped rod, specifically a Z-shaped rod.

Fourth Embodiment

Figure 5:
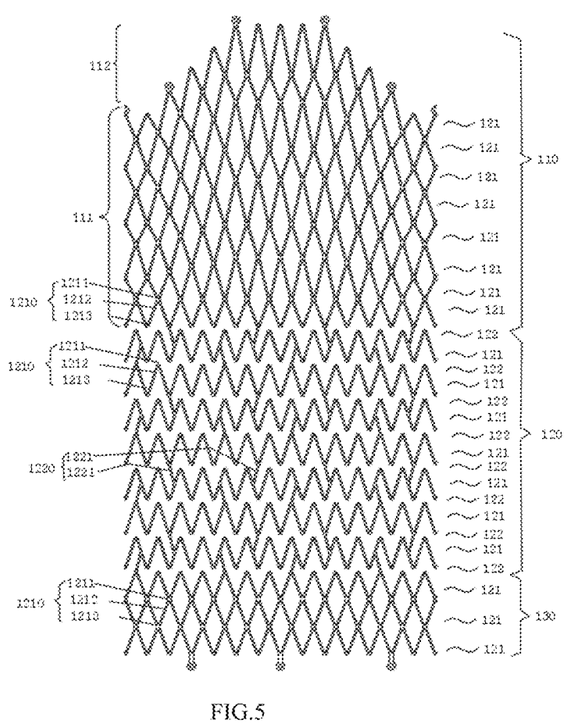
FIG. 5 is a structural schematic diagram of an expanded vascular stent in accordance with a fourth embodiment of the present disclosure.
Figure 5A:
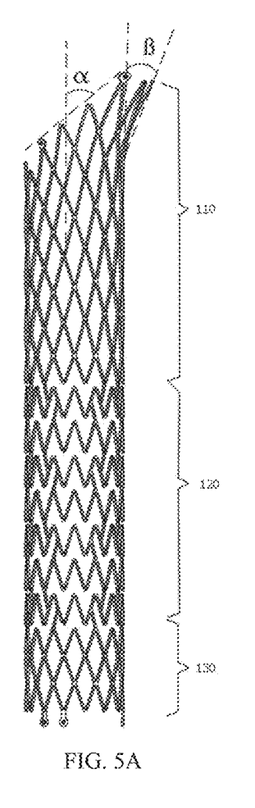
FIG. 5A is a structural schematic diagram of the vascular stent of FIG. 5 in an operating status.

As shown in FIG. 5 and FIG. 5A, the vascular stent of the fourth embodiment is based on the second embodiment or the third embodiment, and is partially improved.

The differences are that the lengths of the wave rods 1212 of the axially connected wave-shaped supporters 121 of the proximal support mechanism 110 are different. At least the amplitude of the wave-shaped supporters 120 of the second support portion 112 gradually increases from the inside to the outside of the vascular stent. In this embodiment, the number of wave rods 1212 in the axial side of the proximal support mechanism 110 is the same, and the length of some inner wave rods 1212 gradually extends in the axial direction toward the proximal end. That is, the number of wave rods 1212 along the axial direction of the proximal support mechanism 110 is the same, and the length of the wave rods 1212 increases gradually from the distal end to the proximal end. In this embodiment, as shown in FIG. 5, the length of the wave rods 1212 on the outer side of the vascular stent has a larger increasing degree, and the length of the wave rods 1212 on the inner side of the vascular stent increases symmetrically and has a smaller increasing degree. Because the amplitude of the waveform of the waveform support 121 is lengthened, a slope is formed on the end surface of the proximal end of the proximal support mechanism 110.

As shown in FIG. 5A, in order to further strengthen the adhesion of the vascular stent to the inner wall of the blood vessel, in the expanded proximal support mechanism 110, at least the second support portion 112 gradually expands from the distal end to the proximal end, that is, while the second support portion 112 begins to extend from the first support portion 111 to the proximal end along the axial direction, it also gradually extends outwardly in the radial direction to form an outward turning bell mouth structure. The degree of outward turning cannot be too large. Preferably, an angle β between the axially longest portion of the second support portion 112 and the central axis of the vascular stent satisfies: 30°≥β>0°, that is, the second support portion 112 is slightly outward. As shown in FIG. 5A, in this embodiment, the proximal end closed-loop region gradually expands outward in the radial direction from the distal end to the proximal end by an angle β of 20°. The tubular structure expands outward at a certain angle at the proximal end, which is more in line with the anatomy of a bifurcated blood vessel, so that the proximal end of the vascular stent can achieve a good adherence effect.

The differences from the third embodiment are that the two connecting rods 1221 of each connecting component 121 are separated by at least two peak units 1211 or two valley units 1213. The connecting components 122 of the three adjacent wave-shaped supporters 121 and the closed-loop connection unit formed by the corresponding wave-shaped supporters 121 have overlapping projection parts on the vertical axial plane, which can better ensure the scalability and connection strength of the vascular stent, and also allow the shape of the vascular stent and the wave-shaped supporter 121 to be maintained in a good shape during the expansion or contraction.

Fifth Embodiment

Figures 6, 6A:
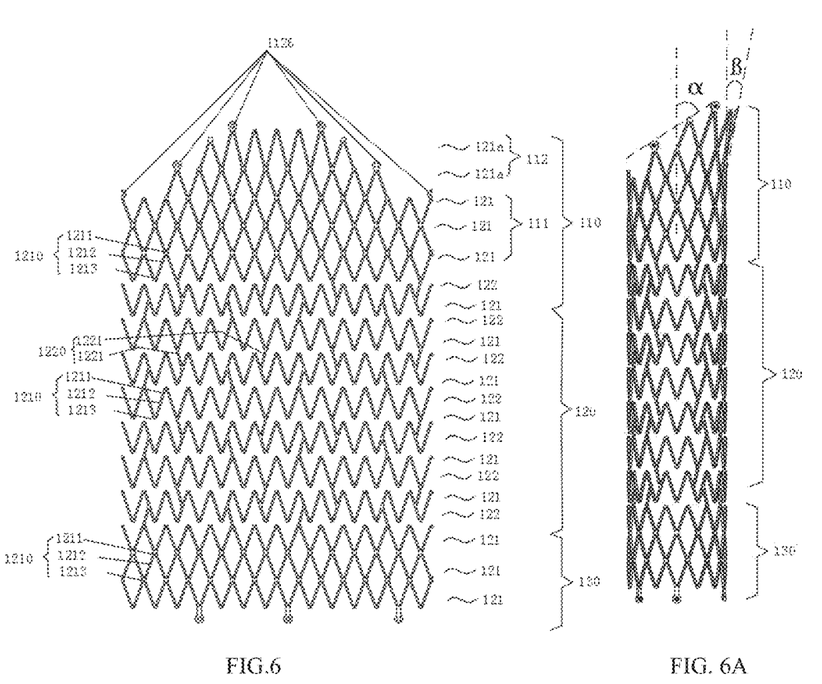
FIG. 6 is a structural schematic diagram of an expanded vascular stent in accordance with a fifth embodiment of the present disclosure.
FIG. 6A is a structural schematic diagram of the vascular stent of FIG. 6 in an operating status.
Figure 7:
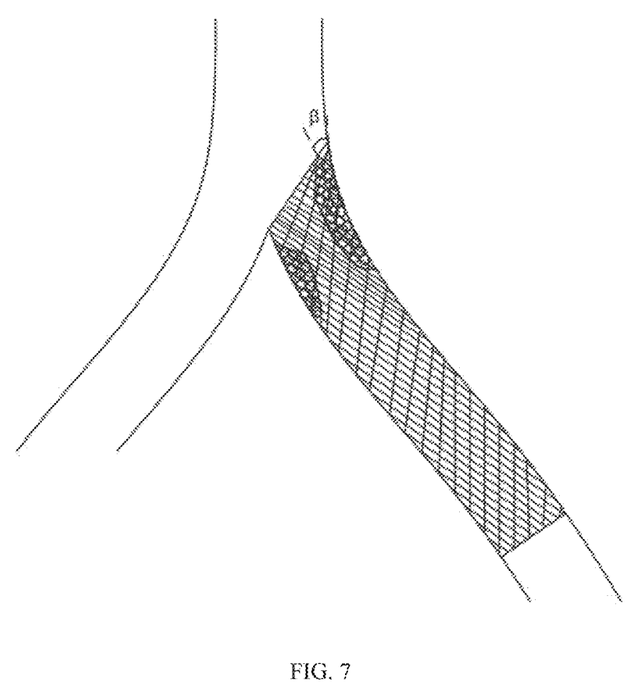
FIG. 7 is a structural schematic diagram of a vascular stent implanted in a blood vessel in accordance with embodiments of the present disclosure.

As shown in FIG. 6 and FIG. 6A, the proximal support mechanism 110 of vascular stent of the fifth embodiment includes a first support portion 111 and a second support portion 112. The structure of the portion is the same as that of the second embodiment, and details are not described herein.

Compared to the fourth embodiment, the grid height is adjusted by adjusting the axial length of the wave rod 1212 of the supporting unit 1210. The inclined end surface of the proximal end of the proximal support mechanism 110 of the fifth embodiment is formed by increasing or decreasing the number of grids, and has grids in more uniform size, with better radial and axial support strength.

In addition, in this embodiment, the proximal support mechanism 110 gradually expands outward in the radial direction from the distal end to the proximal end by an angle β of 10°. The vascular stent expands outward at a certain angle at the proximal end, which is more in line with the anatomy of a bifurcated blood vessel and enables the proximal end of the vascular stent to achieve a good adherence effect.

The above description is only the preferred embodiments of the present disclosure, and is not intended to limit the present disclosure. Any modification, equivalent replacement, and improvement made within the spirit and principle of the present disclosure shall be included within the protection range of the present disclosure.

What is claimed is:

1. A vascular stent comprising a plurality of wave-shaped supporters connected axially, wherein:
    the vascular stent is tubular and comprises a proximal support mechanism, a middle support mechanism, and a distal support mechanism connected in sequence;
    the middle support mechanism and the distal support mechanism are in a closed-loop structure, respectively;
    the proximal support mechanism comprises a first support portion connected to the middle support mechanism and a second support portion provided on a proximal end of the first support portion;
    the first support portion is a closed-loop structure;
    the second support portion is an open-loop structure, and an end surface of a proximal end of the second support portion is an uneven structure to provide regional support circumferentially; and
    the vascular stent further comprises a plurality of connecting components;
    wherein the plurality of connecting components are coupled to some of the plurality of wave-shaped supporters, and any two adjacent wave-shaped supporters of the some of the plurality of wave-shaped supporters are provided with a connection component of one of the plurality of connecting components; an another some of the plurality of wave-shaped supporters are connected to form grids;
    each of the plurality of wave-shaped supporters comprise a plurality of supporting units; each supporting unit comprises a peak unit, a valley unit, and a wave rod in connection between the peak unit and the valley unit; and
    each of the plurality of connecting components comprises at least two connecting rods; one end of each of the at least two connecting rods is connected to the peak unit or the valley unit of a respective wave-shaped supporter, and an another end of each of the respective connecting rods is connected to the wave rod of an another wave-shaped supporter adjacent to the respective wave-shaped supporter; each of the plurality of wave-shaped supporters comprises peak units and valley units that not connected to any connecting rod.

2. The vascular stent according to claim 1, wherein the end surface of the proximal end of the second support portion is an inclined plane, an inclined arc surface, or an inclined wave surface.

3. The vascular stent according to claim 2, wherein the end surface of the proximal end is an inclined plane, and an angle between the end surface of the proximal end and an axis of the vascular stent is a, wherein 90°>α>0°.

4. The vascular stent according to claim 1, wherein an amplitude of the wave-shaped supporters of at least the second support portion gradually increases from an inside to an outside of the vascular stent.

5. The vascular stent according to claim 1, wherein the grids comprises first grids, wave-shaped supporters of the proximal support mechanism have a same wavelength; peak units of adjacent wave-shaped supporters within the proximal support mechanism are connected to valley units to form the first grids; a number of the first grids of at least the second support portion gradually decreases from a distal end to a proximal end; and
    the grids further comprises second grids, a plurality of the wave-shaped supporters of the distal support mechanism are connected to form the second grids; and the plurality of wave-shaped supporters of the middle support mechanism are spaced apart from each other.

6. The vascular stent according to claim 1, wherein the plurality of connecting components comprises first connecting components; the middle support mechanism, the proximal support mechanism, and the distal support mechanism are connected by the first connecting components, at least two connecting rods of the first connecting components are provided at a circumferential interval.

7. The vascular stent according to claim 6, wherein the plurality of connecting components comprises second connecting components; the wave-shaped supporters of the middle support mechanism are connected by the second connecting components, at least two connecting rods of the second connecting components are provided at a circumferential interval.

8. The vascular stent according to claim 7, wherein projections of the first and second connecting components provided between three adjacent wave-shaped supporters on a vertical axial plane do not overlap or partially overlap; or projections of the second connecting components provided between three adjacent wave-shaped supporters on the vertical axial plane do not overlap or partially overlap.

9. The vascular stent according to claim 1, wherein two adjacent connecting rods of the at least two connecting rods angle toward or away from each other.

10. The vascular stent according to claim 1, wherein each of the at least two connecting rods is a straight rod, a special-shaped rod with a curved structure, a special-shaped rod with an arc structure, or a combination thereof.

11. The vascular stent according to claim 1, wherein the wave rod of each of the plurality of supporting units is a straight rod, a special-shaped rod with a curved structure, a special-shaped rod with an arc structure, or a combination thereof.

12. The vascular stent according to claim 1, wherein a part of two adjacent wave-shaped supporters not connected to the plurality of connecting components is suspended.

13. The vascular stent according to claim 1, wherein after the vascular stent is expanded, at least a portion of the proximal support mechanism has a gradual outward flare in a direction from a distal end to a proximal end.

14. The vascular stent according to claim 13, wherein an extending direction of the gradual outward flare and an axis of the vascular stent forms an angle $\beta$, and the angle $\beta$ satisfies: $30° \geq \beta > 0°$.

15. The vascular stent according to claim 1, wherein after the vascular stent is expanded, an outer diameter of the vascular stent gradually expands from a distal end to a proximal end to form a cone structure.

16. The vascular stent according to claim 1, wherein a plurality of support points are provided on a proximal end of the stent proximal support mechanism and/or a distal end of the distal support mechanism.

17. The vascular stent according to claim 16, wherein each support point is a hollow structure, and a radiopaque marker is provided inside the hollow structure.

18. The vascular stent according to claim 1, wherein two wave rods of each the plurality of wave-shaped supporters connected to two adjacent connecting rods of each of the plurality of wave-shaped supporters are arranged at an interval.

19. The vascular stent according to claim 1, wherein the plurality of connecting rods are spirally arranged or staggered in an axial direction of the vascular stent along a length of the vascular stent.

* * * * *